(12) United States Patent
Buchner et al.

(10) Patent No.: US 10,852,296 B2
(45) Date of Patent: Dec. 1, 2020

(54) MICRO-SAMPLING FOR CELL, TISSUE, AND MICRO-ORGANISM MONITORING

(71) Applicant: BiOMICom Incorporated, Allison Park, PA (US)

(72) Inventors: James D. Buchner, Pittsburgh, PA (US); Ross C. Willoughby, Pittsburgh, PA (US)

(73) Assignee: BiOMICom Incorporated, Allison Park, PA (US)

( * ) Notice: Subject to any disclaimer, the term of this patent is extended or adjusted under 35 U.S.C. 154(b) by 484 days.

(21) Appl. No.: 13/728,865

(22) Filed: Dec. 27, 2012

(65) Prior Publication Data
US 2016/0282333 A1    Sep. 29, 2016

Related U.S. Application Data

(60) Provisional application No. 61/631,050, filed on Dec. 27, 2011.

(51) Int. Cl.
*G01N 33/50* (2006.01)
*C12M 1/00* (2006.01)

(52) U.S. Cl.
CPC ..... *G01N 33/5023* (2013.01); *G01N 33/5005* (2013.01); *C12M 47/04* (2013.01); *C12M 47/06* (2013.01); *G01N 33/5082* (2013.01)

(58) Field of Classification Search
CPC ... C12M 25/14; C12M 47/04; G01N 33/5082; G01N 33/5023
See application file for complete search history.

(56) References Cited

U.S. PATENT DOCUMENTS 5,473,952 A    12/1995    Lieberman et al.
5,808,300 A     9/1998    Caprioli
5,993,649 A    11/1999    DeBusk et al.
(Continued)

OTHER PUBLICATIONS

Boardman et al., "The interface of an array of five cappilaries with an array of one-nanoliter wells for high-resolution electrophoretic analysis as an approach to high-throughput chemical cytometry", Anal. Chem., 2008, pp. 7631-7634, vol. 80, No. 19.
(Continued)

*Primary Examiner* — Jonathan M Hurst
(74) *Attorney, Agent, or Firm* — The Webb Law Firm (57) ABSTRACT

Cell and organ (or tissue) cultures provide a micro-environment with respect to nutrients, gas exchange, and scaffolding in order to encourage specific cell function, and in some cases to mimic in-vivo cellular expression under in-vitro conditions. We describe apparatus and methods to chemically, spatially, and temporally measure diffusible molecules produced, or used by cells or tissues in culture. In this manner, mechanisms of cell-cell interaction and other chemical signaling, detailed biochemical pathways, and the action of potential pharmaco-therapy agents can be better understood at a molecular level. In addition to basic science, the technical advantages of process monitoring and control can be applied to optimize culture products in bioreactors. Embodiments of this device are intended to simulate and monitor [input and output] the behavior of vascular capillary beds in higher species vascular systems.

23 Claims, 9 Drawing Sheets

(56) References Cited

U.S. PATENT DOCUMENTS

| | | |
|---|---|---|
| 7,442,927 B2 | 10/2008 | Fedorov |
| 7,831,075 B2 | 11/2010 | Wilson et al. |
| 9,188,512 B2 | 11/2015 | Van Mooy et al. |
| 2004/0261143 A1 | 12/2004 | Mumm et al. |
| 2006/0154361 A1* | 7/2006 | Wikswo ............ B01L 3/502746 435/289.1 |
| 2007/0031962 A1 | 2/2007 | Levin |
| 2009/0026092 A1 | 1/2009 | Reardon et al. |
| 2009/0098541 A1* | 4/2009 | Southern ........... B01L 3/502753 435/6.11 |
| 2009/0221014 A1 | 9/2009 | Reardon et al. |
| 2013/0244250 A1 | 9/2013 | Yang et al. |
| 2013/0298702 A1 | 11/2013 | Lam et al. |

OTHER PUBLICATIONS

Gong et al., "On-line Sample Preconcentration Using Field-amplified Stacking Injection in Microchip Capillary Electrophoresis", Anal. Chem., 2006, pp. 3730-3737, vol. 78, No. 11.

Hu et al., "Asymmetry between Sister Cells in a Cancer Cell Line Revealed by Chemical Cytometry", Anal. Chem., 2004, pp. 3864-3866, vol. 76.

Jung et al., "Thousandfold signal increase using field-amplified sample stacking for on-chip electrophoresis", Electrophoresis, 2003, pp. 3476-3483, vol. 24.

Wang et al., "Direct Sampling from Human Liver Tissue Cross-sections for Electrophoretic Analysis of Doxorubicin", Anal. Chem., 2009, pp. 3321-3328, vol. 81, No. 9.

Elsdon et al., "Spatial and temporal monitoring of coastal water quality: refining the way we consider, gather and interpret patterns", Aquatic Biology, 2009, pp. 157-166, vol. 5.

\* cited by examiner

Fig 1

| Patent Component | Alternatives | |
|---|---|---|
| Input media | 1. Reagents<br>2. Nutrients<br>3. Drugs<br>4. Gases (e.g. Respiration)<br>5. Blood<br>6. Output from upstream cultures<br>7. Output from natural environment (e.g. lake, stream)<br>8. Buffers<br>9. Stimulants- induced response<br>10. Retardants- inhibits response<br>11. Pollutant | Alternate embodiment- monitor input media directly for both informational and/or feedback control purposes. |
| Input means | 1. Pumped fluid stream<br>2. Pumped fluid stream across selective aperture array<br>3. Pumped fluid stream across membrane or fritted interface<br>4. Conductance via diffusion across selective membrane<br>5. Conductance via electrodynamic forces across electrostatic aperture array- gas or liquid<br>6. Convection supplying material to input barrier<br>7. Input barrier such as membrane, tube, array, or other selective materials (e.g. artificial skin)<br>8. Bundles of permeable tubes that are interspersed within the sample volume | |
| Sample | 1. Cells<br>2. Tissues<br>3. Micro-organisms<br>4. Cell Cultures<br>5. Tissue Cultures<br>6. Viruses<br>7. Bacteria<br>8. Collected samples from environmental sources (e.g. biohazards or bio agents)<br>9. Cells supported upon a substrate material.<br>10. 2D gels containing biological sample components (e.g. cell lyse sample)<br>11. Non-biological samples where 2D or 3D imaging is required | |
| Output means | 1. Aperture arrays<br>2. Addressable aperture arrays- mechanical<br>3. Addressable aperture arrays- electrostatic<br>4. Frits<br>5. Filters<br>6. Tubes<br>7. Permeable tubes<br>8. Membranes<br>9. Bundles of permeable tubes that are interspersed within the sample volume | |
| Monitoring means for characterizing output materials; including, products of metabolism and residual input media. | 1. Sample collection devices such as liquid pumping or pressure differentials<br>2. Sample separation devices such as chromatography and extraction (e.g. SPE), electrokinetic.<br>3. Sample component analysis with mass spectrometry, ion mobility, or any number of alternate molecular detection technologies.<br>4. Sample component analysis with absorption or emission spectroscopy. | |

| State | V1 | V2 | Q1 | P1 | V3 | V4 | Q2 | P2 | V5 kV | Comment |
|---|---|---|---|---|---|---|---|---|---|---|
| Idle | 0 | 0 | + | + | 0 | 0 | + | ++ | -6 | Culture media and solutes exiting the cell flow to vent radially at the observation barrier:addressable array 1 gap at P1 backpressure; a suitable solvent is delivered at the gap between the two addressable arrays at a pressure P2 where P2>P1, where solvent flows both to vent with the media and through to the spray nozzle |
| Load solute | -- | - | 0 | 0 | 0 | 0 | + | + | -6 | Media flow from the peristaltic and from the exit at the observation barrier:addressable array 1 gap is momentarily turned off. Positive ions and polar migratory neutrals loaded into the entrance of addressable array 1 using V1 bias for those array addresses to be sampled; lateral diffusion from adjacent regions may be rejected using bias on surrounding holes; loading period can be extended for solute concentration; further migration reduced using V2 bias at the exit side of the selected channels |
| Solute transfer | ++ | + | 0 | 0 | 0 | 0 | + | + | -6 | Solutes migrate to addressable array 2 by electroosmotic flow and electrokinetic motion; V1 & V2 can be programmed to separate components according to their electrophoretic properties |
| Solute separation | ++ | + | + | + | - | -- | + | ++ | -6 | Further separation can occur on addressable array 2 with media flow through the culture volume on; solvent composition or ionic strength can be varied to suit needs of separation |

Fig 6

MICRO-SAMPLING FOR CELL, TISSUE, AND MICRO-ORGANISM MONITORING

CROSS-REFERENCES

This application is entitled to the benefits of Provisional Patent Application Ser. No. 61/631,050 filed on Dec. 27, 2011 and Ser. No. 61/688,884 filed on May 24, 2012.

FIELD OF INVENTION

This invention pertains to the chemical and bio-molecular testing and control of cellular behavior to characterize composition and production of chemical species from cellular activity.

BACKGROUND OF THE INVENTION

The value of molecular imaging tissue samples has been demonstrated using a variety of spectroscopic methods including mass spectroscopy (MS). Currently, the use of MS for tissue imaging is largely on "dead" tissue cross-sections using matrix assisted laser desorption ionization (MALDI) (1). In these methods a laser with sufficient power and small focal point is rastered across a tissue surface coated with a chemical matrix which assists in desorption and ionization of bio-molecules. These methods are being widely used with success in a number of biomedical applications. The nature of MALDI methods is such that the cells are not living and the chemical map obtained is, at best, a static reflection of the local chemistry immediately prior to cell death. These methods do not permit the study of cellular expression products resulting from growth and cell-cell interaction on a continuing time scale. In addition, the opportunities to use external stimulae of the system to study their effect on cell phenotype, growth, and expression are lost.

Work in the area of chemical cytometry has addressed some specific analysis problems at the level of single cell measurement. Krylov et al (2) used two channel chemical cytometry to study asymmetric patterns of protein expression in sister cells of a cancer cell line. Capillary zone electrophoresis (CZE) with laser induced fluorescence detection was used on isolated single sister cells to observe patterns in green fluorescence protein expression. The work of Krylov et al was extended by Dovichi et al (3) to the use of a five capillary array sampling of isolated AtT-20 cells in nanoliter wells. A series of metabolites from a substrate molecule were studied using capillary electrophoresis. In these proof-of-principle experiments the system was used to generate five CZE electropherograms simultaneously to support high throughput chemical cytometry measurements.

Arriaga et al (4) performed direct sampling of components from human liver cross-sections for electrophoretic analysis. Samples were directly aspirated from both tissue and gelatin surfaces using an etched tip capillary. After sampling, the analysis was performed using micellar electrokinetic chromatography (MEKC) and fluorescence detection. The work was directed at the detection of doxorubicin (Dox), a chemotherapy drug, and its metabolites after chemoembolization of the liver of a hepatocellular carcinoma patient. Tissue cross-sections of 5 um were obtained from the explanted liver using a cryomicrotome. Tumor and non-tumor regions were determined based on tissue histology. Heterogeneous distribution of the parent drug with some metabolites was found. Sampling resolution was shown to be as close as 100 um. The work was limited due to the maintenance of viable tissue during the sequence of measurements. The use of capillary arrays was suggested as a potential future improvement to perform simultaneous measurements.

Wilson et al (5) have integrated histologic and analytical measurement systems directly into a cryomicrotome with x-y translation. Cryo-imaging bridges the gap between whole animal in vivo imaging (with the expanded modality from CT, PET, MRI, ultrasound measurement) and histology. Samples as large as whole mice are frozen and sectioned. Each section can then be studied sequentially using a variety of optical and fluorescence methods on both microscopic and macroscopic levels. The distribution of a dosed and appropriately tagged molecule prior to animal sacrifice can be mapped to support the measurement of levels of target expression or receptor occupancy in pharmacokinetic studies. This work is generally in the critical path of bringing a therapeutic drug to market. The development of appropriate surrogate probes or imaging agents to map the biodistribution of the drug is often considered when the drug molecule itself is designed.

A scanning ion probe system that uses a reverse Taylor cone ionization region has been developed by Fedorov (6) having potential to perform chemical imaging of biological samples. In this method, a sample contained within an electrolytic medium is biased at a voltage. The sample is also proximate to a sharp electrode (ion probe) which is in turn is biased and in communication with a hole array membrane. Under these conditions, ions formed in solution comprise part of a reverse Taylor cone formed at the opposite side of the membrane. The droplets are desolvated resulting in ion evaporation with the ions then analyzed using a number of different methods, including MS. The ion probe can be can be translated in the x-y plane in order to chemically image a sample surface. Since a bias potential must be applied to the sample to obtain ions, any tissue or cell based measurements would likely involve dead biomass.

The present invention while not focused primarily on observing the individual cell spatial domain, maintains the ability to observe processes of living cell aggregates, and the interaction of cells of varying phenotype in culture. In this manner molecular species that are involved in short range cell-cell signaling and specific metabolic biomarkers for disease states can be more readily characterized. In addition, the culture system can be actively probed using various external stimulae such as growth factors and potential pharmacotherapy agents to determine cause and effect relationships as well pharmacokinetic parameters during "real-time" chemical characterization.

The culture of cells in-vitro can be viewed as roughly split into two methods, organ culture and cell culture (7). There are unique benefits as well as problems associated with each type of culture method from both operational and informatic perspectives. In organ culture the architecture of the tissue is maintained through the use of aggregated tissue that retains, at least in part, the three dimensional shape and the histologic features of the tissue in-vivo. However, maintenance of the physicochemical and physiologic conditions required for organ culture are difficult. Cell cultures on the other hand are derived from dispersed cells taken from original tissue or from isolated cell lines and are much easier to maintain. Mature cell cultures that grow and re-aggregate to assume a three dimensional structure are often referred to as a histotypic culture. When different cell lines are recombined in culture in an attempt to generate a tissue equivalent the resulting culture is often referred to as an organotypic culture.

External support systems are required by all in-vitro cultures to provide a favorable micro-environment to sustain cell viability and growth. The micro-environment is a combination of physio-chemical and physiologic factors, the basic design of the culture assembly for nutrient and gas exchange, and the nature of the cell support (scaffold) to promote adherence and three dimensional growth. Physio-chemical parameters include the control of pH, temperature, osmolality, and the partial pressures of dissolved gases. Physiologic parameters include control of nutrients, hormones, and other biologic co-factors. Due to the lack of a vascular system in-vitro mammalian cell aggregates of around 250 um and larger are diffusion limited. Mammalian cell aggregates of 1 mm or larger often result in central necrosis if there is not adequate provision for both nutrients and gas exchange. Gas exchange is important to maintain an acceptable range for the partial pressures of oxygen and carbon dioxide to support cellular respiration and pH. Nutrient provision also effects pH but in addition provides essential molecules for the cell to use for energy, growth factors, proteins, minerals, and the overall osmolality of the culture. When the objective is to mimic in-vivo conditions, ideally, the nutrient system is a direct replacement for the extracellular matrix (ECM) including the normally secreted endocrine hormones. Practically, due to cost and availability it has been more common to use either bovine serum albumin (BSA) or fetal bovine serum (FBS) as a source of nutrients for cell culture systems. Quite often these sources are supplemented with other co-factors such as steroid hormone growth factors or other proteins to more adequately mimic the physiologic micro-environment of the in-vivo cell system.

In cell culture, after inoculation, the development of higher cell densities that approach histotypic is time dependent, often taking weeks or months depending on the cell type and micro-environment. Cell-cell interaction in a developing histotypic or an organotypic culture is initially manifested as a result of contact mediated signaling which further results in the formation of gap junctions and the exchange of homocrine factors. The early stage of this contact is evidenced by reduced cell motility, at least in part due to contact inhibition, and withdrawal from the cell cycle due to density limitations of cell proliferation. Where cells have the ability to differentiate there is often an increase in the proportion of differentiated cells.

The design of organ and cell culture assemblies varies considerably. Diffusion limitations have led to many mammalian organ culture designs consisting of an open well where the tissue sample is supported on a filter pad at the surface of a pool of nutrient. With rocking, the sample undergoes alternating exposure to gas and nutrients to facilitate adequate exchange. Organ culture using explanted tissue samples has often used this type of culture apparatus. Filter well culture apparatus permits many cultures to be run in parallel, 96 well systems are common, which have facilitated adsorption, distribution, metabolism, elimination, and toxicology (ADMET) studies for drug development. Many filter well systems and flask-based systems allow cell growth at membrane surfaces or in suspension. Perfusion based systems are generally closed systems with a three dimensional scaffold inside the active volume for cell attachment and growth in the case of a cell culture. Generally a peristaltic pump is used to move nutrients and other co-factors through the culture and to an exit in the active volume. These types of systems also often provide for gas transport across a permeable membrane. A variant in this design is the hollow fiber perfusion bio-reactor (HFPB) where cell growth and adhesion is to and around the outside radii of an array of thousands of hollow fibers through which flows nutrients, co-factors, and dissolved gases. The diameter of the fibers is of the order of 100 um and the composition and porosity of the fibers can be varied to influence critical exchange of raw materials for waste products.

With regard to organ culture, current cryomicrotome equipment can routinely produce tissue sections from 0.5 to 100 um. The use of cryosections has the additional advantage of maintaining tissue integrity relative to other methods. In organ culture, cells are fully differentiated and cell-cell interaction may be studied in a state more representative of in-vivo function. Of course, this is predicated by the support of the culture with perfusion of a surrogate ECM or serum and effective gas exchange.

The field of cell and organ culture supports a wide array of basic and applied areas of application. In addition to basic studies of cell-cell interaction, cellular metabolism, the regulation of gene expression and phenotype at various stages of development, extensions of these methods into immunology, pharmacology, toxicology, and tissue regeneration and transplantation promise to make this work key in understanding normal development and pathological aberrations.

SUMMARY OF INVENTION

Acquiring biochemical and physical information relating to the activity of cells, tissues, and micro-organisms is difficult because of difficulties with spatial, temporal, and compositional measurements at the dimensions that processes occur. Extracting and isolating chemical components from living systems often involves the destruction of the cells and tissue in so-called blender chemistry methods that lead to significant limitations in the quality of the result. Spatial resolution is lost, chemical structures can be altered, and temporal studies of tissues are limited or cumbersome. There is a need for higher spatial precision for sample collection, higher sensitivity for measurements at the cellular level, and higher temporal measurements for studies of cell specific behavior. In addition, the preservation of cellular activity in a non-destructive cultured environment will yield enhance information content for structure and function relationships.

The present invention is intended to provide an alternative to blender chemistry whereby cells, tissues, and micro-organisms can be isolated and preserved onto a sample holding substrate in order to provide enhanced control and measurement of input media to the sample, and enhanced control of output collection and monitoring for measurements of biological activity. The use of micro-fabricated addressable arrays allows precise control of mass transfer both into and out of sample regions with high spatial and temporal control. The present device includes all of the embodiments of macroscopic process control with the advantage of operation at the dimensions of the individual cells and tissues. Embodiments of the present device have advantages for delivering nutrient and stimulant media to both 2-dimensional substrates and 3-dimensional substrates.

We envision the use combinations of enrichment chromatography with high efficiency ionization and transmission mass spectrometry as a primary monitoring alternative. The mass spectrometer inherently has some of the highest levels of selectivity, sensitivity, specificity, and speed to facilitate rapid results with high information content.

BRIEF DESCRIPTION OF DRAWINGS

FIG. 2—Table itemizing alternative embodiments for each major component of the system. Although the present invention comprises the components in FIG. 1, there are a large number of differing embodiments of the device that enable unique operation and novel applications.

FIG. 3—A preferred embodiment of the invention showing an input media being delivered from an input reservoir using a peristaltic pump. The input means delivering input media to sample cells, tissue, or micro-organisms is accomplished by selective transfer to the cells through the ports of an aperture array. The output means in this embodiment is the combination of a selective membrane and selective aperture array that delivers at least some of the products of biological activity from the sample. Spatial and temporal sampling of product output can be accomplished by manual collection across discrete outlet apertures or by use of automated a mechanical translation device. In this embodiment, the output is delivered to a switching valve for sample preparation, chromatographic and mass spectrometric analysis.

FIG. 4—An alternative preferred embodiment of the invention uses additional stages of transfer for further conditioning of the sample output in order to make sample compatible with monitoring requirement. Here the input media is delivered from one or more input reservoirs using one or more peristaltic pumps. The input means is provided by a selective aperture array in order to provide spatial and temporal control on input media to the sample region. The output means in this embodiment is one or more addressable arrays provide spatial and temporal control of sampling to the sample output products delivered to a monitoring means. In this embodiment, the switching system is coupled to chromatography-mass spectrometry and provides enrichment, selectivity, and specificity for the output product monitoring. Multiple input means are illustrated as an alternative which allows for input media to be applied both generally and specifically to the input surface of the entrance aperture array. A plurality of input means can be used for selective input to the sample.

FIG. 5—An alternative preferred embodiment of the invention showing an input media delivered from an input reservoir using a peristaltic pump. This embodiment has similar input and sample components but alternatively utilizes an addressable electrospray array that generates spatial and temporal control of the production of gas-phase ions through the electrospray process. The ions produced by the addressable electrospray array are delivered directly to a mass spectrometer through optical and conductance means. Additional stages in this embodiment may alternatively include conditioning of sample streams to desalt, enrich, separate, and further modify the sample downstream from the sample region with mobile phase components, buffers, modifiers, electrolytes, and ion-pairing reagents. Downstream modification is intended to be completely isolated from the sample environment as to not effect the biological activity of the sample.

REFERENCE NUMBERS IN DRAWINGS 1 input media
2 input means
3 sample
4 output means
5 monitoring means
6 media reservoir
7 peristaltic pump
8 media input
9 entrance aperture array
10 culture volume
12 membrane
14 observation barrier
16 product output
18 product sampling pump
20 sample conditioning means
22 chromatograph
24 mass spectrometer
26 mechanical positioning means
28 addressable array 1
30 addressable array 2
32 movable sampling apertures
34 non-select channel bypass
36 media or solvent outlet
38 solvent input
40 output preconcentration
42 output cleanup
44 electrospray needle array
46 electrospray counter-electrode array
60 permeable tube
62 permeable tube union
64 monitoring stream input media and means 66 output of input stream
70 optional recirculation loop for input media
72 optional recirculation loop for monitoring stream
74 optional monitoring of monitoring stream input (feedback control of flow and composition is optional as well)
76 optional monitoring of input stream inlet (feedback control of flow and composition is optional as well)
78 optional monitoring of outlet of input stream (feedback control of flow and composition is optional as well)
80 Sample molecule source
82 Simulated ion trajectories
84 Equipotential lines
90 Laminated Array
92 Upstream electrode layer
93 Intermediate electrode layer
95 Discrete electrodes
95a Discrete electrode a
95b Discrete electrode b
95c Discrete electrode c
95d Discrete electrode d
96 Downstream electrode layer
97 Control means
100 Top View of Simple Aperture Array

DESCRIPTION OF EMBODIMENTS

Figure 1:
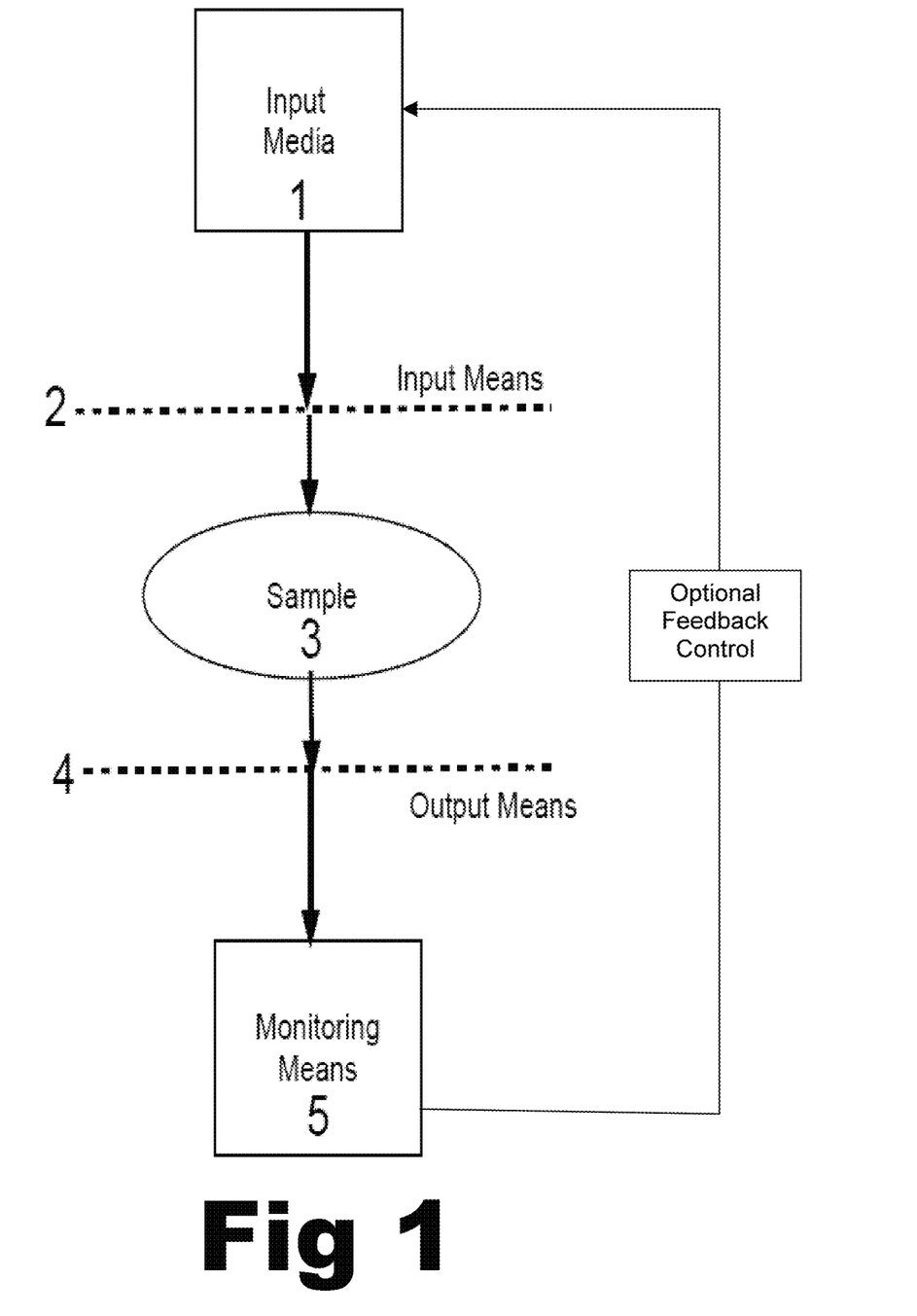
FIG. 1—Flow diagram of the major components of the cell monitoring system. These components comprise an input media, an input means, a sample (cells, tissue, or micro-organisms), an output means, and a monitoring means.

The current invention describes devices and methods intended to monitor (and additionally) control the behavior of selected samples of cells, tissues, or micro-organisms. The invention comprises; a controlled input media delivered to a selected sample 3. Said input media is delivered by an input means 2 in order to elicit or stimulate a response from the said sample or simply provide nutrients to just develop stasis of the sample cells. FIG. 1 is intended to illustrate the general flow of input media 1 to the sample 3, whereby the output from the sample is collected by an output means 4 and monitored by one or more monitoring means 5. Said media 1 is delivered to said sample 3 by one or more input means 2. A wide variety of alternatives embodiments for each component in FIG. 1 are listed in FIG. 2. We envision that this invention will input a variety of input media 1; including but not limited to, reagents, nutrients, drugs, gases, blood, output from upstream cultures, output from a natural environment, buffers, stimulants, retardants, and pollutants. We envision that the variety of embodiments of this invention will utilize a number of alternative input means; including, pumped fluids streams, pumped fluid streams across an aperture array, pumped fluid streams across a membrane or fritted interface, conductance via diffusion across selective membrane, conductance via electrodynamic forces across electrostatic aperture array, convection supplying material to input barrier, input barrier such as membrane, tube, array, or other selective material (e.g. artificial skin), but not limited to bundles of permeable tubes that are interspersed within the sample. The sample 3 intended for evaluation and control with this invention includes, but is not limited to cells, tissues, micro-organisms, cell cultures, tissue cultures, viruses, bacteria, collected samples from a biological (e.g. bio-hazards or bio agents), and cells supported upon a substrate material. The products of biological activity resulting from said sample responding to said input media is collected by output means 4 and delivered to monitoring means 5. The said output means of this invention is envisioned to comprise one or more alternatives; including, aperture arrays, addressable aperture arrays (mechanical), addressable aperture arrays (electrostatic), frits, filters, tubes, permeable tubes, membranes, but not limited to bundles of permeable tube. It is a primary intention of this invention to monitor the output collected from the said sample via the output means 5. Alternatives for monitoring said sample output involve collection, separation, and detection of one or more components of the sample output stream, including, but not limited to chromatography, mass spectrometry, electrophoresis, spectroscopy, and electrochemistry.

This invention generally describes a means of controlled input of input media that are intended to induce or stimulate a response from a given sample cell, tissue, or organism. The result of the high precision with respect to flow, positioning, and composition of input media enables the evaluation of sample bio-activity by monitoring the output products of biological behavior. Precise spatial and temporal control and measurement of both input and output components results in unique information regarding the behavior of the sample cells by direct or differential measurement. Alternatively, monitoring output products from sample cells can also be used to feedback and control the input media (or medias) in order to control the output of the sample cells. There is no limit to the combination of input media components in terms of composition and flow from single or multiple input streams.

Example 1: Preferred Embodiment—(Simple Laminate)

Figure 3:
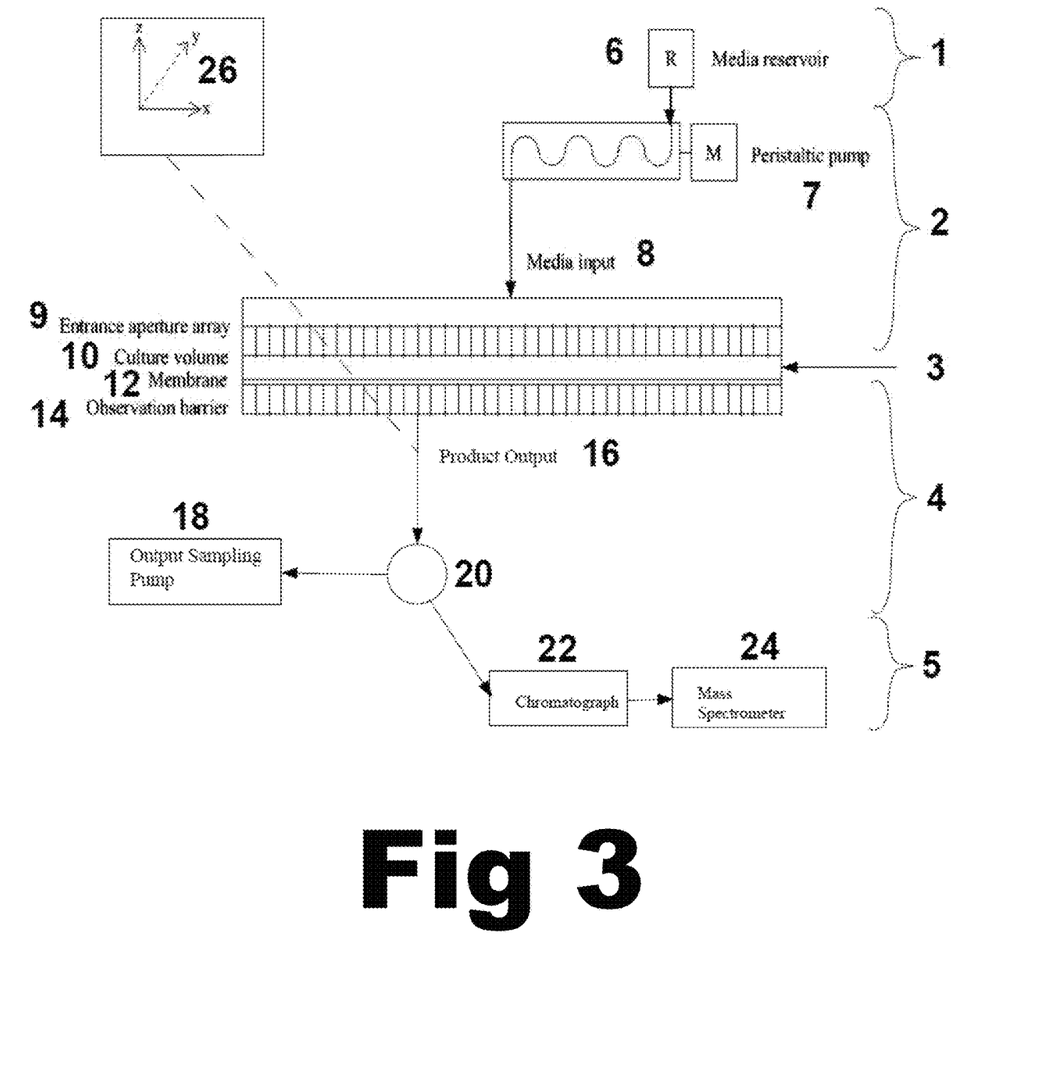

A preferred embodiment is schematically illustrated in FIG. 3. The media reservoir 6 containing input media 1 is delivered to sample 3 by input means 2 comprising a peristaltic pump 7. The media input 8 is delivered through entrance aperture array 9 to culture volume 10 containing sample 3. Said sample comprising cells, tissues, or micro-organisms respond to said input media with biological activity that results in both absorption of at least some of the input media and subsequently the output of products of said biological activity. The output products are passed through membrane 12 through observation barrier 14. Said barrier comprising an array of apertures direct the product output 16 toward downstream chemical or physical monitoring means 5. The said output is directed to sample conditioning means 20 via output sampling pump 18. Sample output monitoring is accomplished by separating output components with chromatograph 22 and analyzing with mass spectrometer 24. We envision no restriction on the breadth of alternatives for chromatographic separation or mass spectrometry analysis; including, but not limited to MS/MS, ICP/MS, GC/MS, LC/MS, IC/MS, and any number of parallel or serial techniques that are used to characterize both organic and inorganic species resulting from biological activity. Additionally, this embodiment is intended to incorporate mechanical positioning control 26 of both media input 8 and product output 16. These components facilitate the positional and temporal control of both input of input media to the sample and output of product output.

One operation of this assembly uses two aperture arrays 9 and 14 to define an active organ or cell culture volume 10 is shown as viewed from the z-axis. A reservoir of oxygenated nutrients and other co-factors is delivered to the culture assembly through the action of a peristaltic pump 6. One array is used to disperse oxygenated nutrient evenly into the active culture volume. This active volume can be of any configuration including a void volume, or scaffolding or tube arrays of any type. The exit from the culture volume in FIG. 3 consists of a membrane supported by an aperture array. Each hole in the array is a receiver for flow of liquid phase that is a composite of the components externally added to the system in excess of that used by the cells, plus the components generated by the cells in culture local to that particular exit hole. The flow from these holes when analyzed individually and the resulting data reassembled constitutes a chemical map of the diffusible molecules consumed and generated in a specific area of the culture. This map may be used in combination with the histology of the sample in organ culture, or with the various cell lines used in cell culture. The net balance of components consumed and produced can in experimental design be compared with variations in physiologic and physiochemical conditions.

In the case where the histology or inoculation regions are known and chemical relationship information reflecting those regions is sufficient, it may be most straight-forward to analyze a limited number of the hole flows in a discrete fashion. In this case, small capillaries may be inserted into the hole array at selected addresses to remove a portion of the liquid flow outside the assembly.

Alternatively, the apparatus may be capable of translation in the x-y plane with respect to discrete sampling apertures. The discrete sampling apertures maintain sealing surfaces such that the flow from target sample points can be individually diverted or combined for any number of purposes. The locations of these sampling apertures may be varied in relation to the culture volume and one another. The use of multiple sampling tubes or apertures allow for the study of event driven chemical changes and their kinetics as a function of cell type and cell-cell interaction. These measurements are also important to facilitate the determination of potential reactive metabolites in the drug development process.

When discrete samples for hole locations are produced, a variety of traditional sample preconcentration, cleanup, separation methods and analytical instrument sample introduction designs can be used for on-line process level measurements. Biological matrix samples are very complex and sample conditioning, such as solid phase extraction techniques, are important to enrich certain components in preference to others.

Example 2: Alternate Preferred Embodiment—(Additional Stages of Conditioning)

Additional stages of sample conditioning may be interposed after the observation barrier but within the device prior to analysis. A plurality of aperture arrays can be positioned downstream from the observation barrier with gaps between which constitute a gate or switch. Sample may be selectively moved across stages (gaps) using hydrostatic (pressure), electrokinetic (voltage), or other mechanical means (valves) of gating sample. In the case of electrokinetic sampling the internal hole surface can be tailored using surface coating materials to establish a dielectric where a voltage drop across the two outside x-y planes of the array can be established. The inside structure of the hole can also be modified to include membranes, porous plugs, stationary phases, etc. to achieve desired conditions for solute migration. The rims of each hole on each x-y plane can be metalized and traced to edges for addressing individual channels. The array of holes are individually addressable such that a potential can be applied to a selected channel, or set of channels, where solutes are sampled preferentially from designated channels in the observation barrier array and advanced through the train. The sampling aperture arrays can also be used to achieve analyte mixture separation or sample preconcentration using electrophoretic or field amplified sample stacking (FASS) methods (8,9). These means can be used in combination with control of both pressure and flow, including stop flow.

Figure 4:
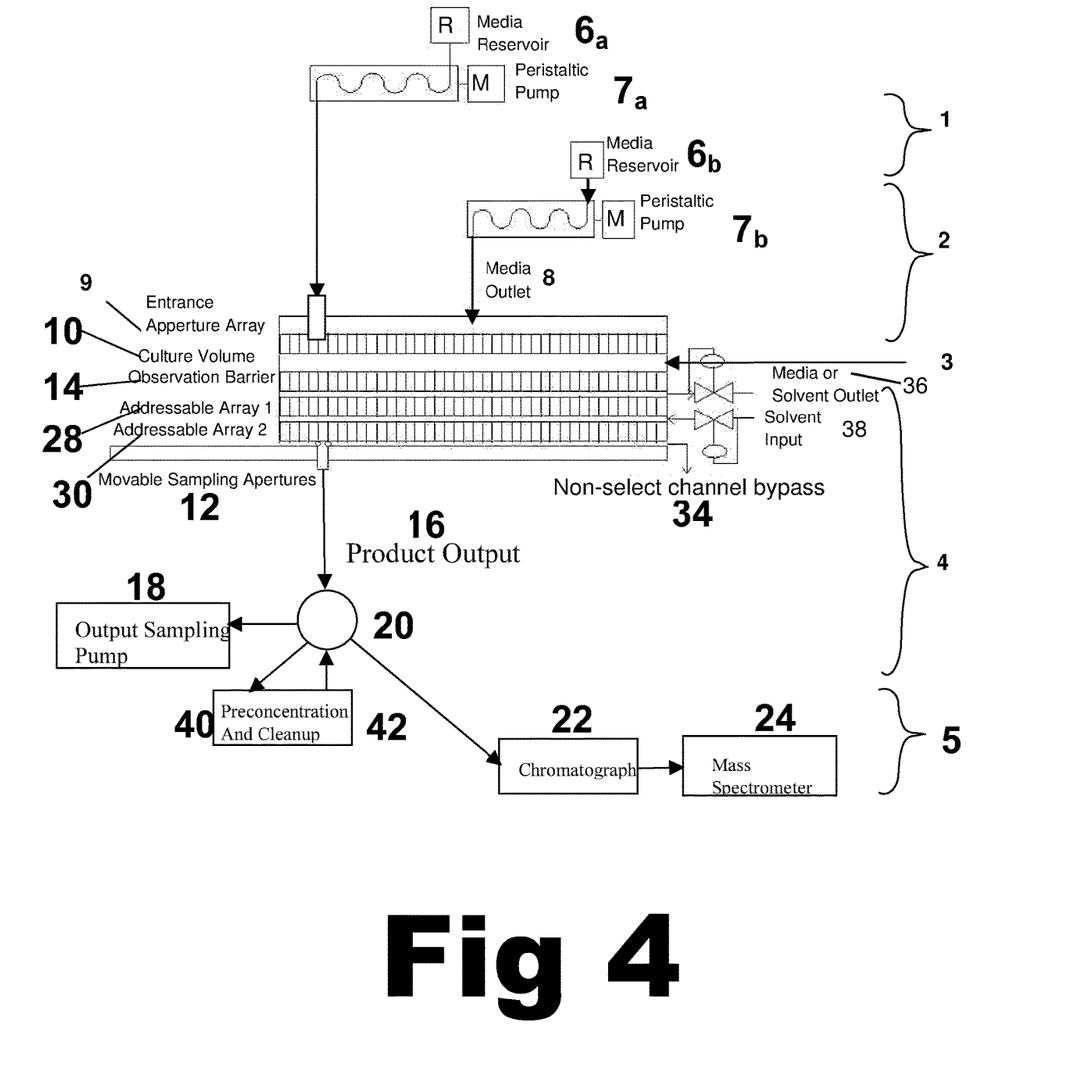

This alternate preferred embodiment with additional stages is schematically illustrated in FIG. 4. The media reservoirs 6a and 6b containing input media 1 can selectively and independently deliver differential media to sample 3 by input means 2 comprising peristaltic pumps 7a and 7b. The media is delivered through entrance aperture array 9 to culture volume 10 containing sample 3. Said sample comprising cells, tissue, or micro-organisms respond to said input media with biological activity that results in both absorption of at least some of the input media and subsequently the output of products of said biological activity. The output products are passed through observation barrier 14 whereby output media is directed toward media or solvent outlet 36. This direction of flow can be facilitated by downstream pumping. Some of the products of bio-activity of sample cells may directed away from outlet 36 flow by being induced to pass through addressable array 28. The product species can be induced to flow across the addressable array by electrostatic forces, mechanical forces, and/or pressure. At the downstream side of the addressable array 28 solvent input 38 is accomplished to condition the sample for detection with the mass spectrometer. Solvent input 38 may comprise a wide variety of solvent and solvent modifier alternatives. Said input 38 entrains the product output from addressable array 28 and directs the flow through addressable array 30 to be sampled for downstream monitoring through movable sampling aperture 12 resulting in product output 16. The product output 16 is directed to sampling valving means 20 under the influence of output sampling pump 18. In this embodiment, the conditioning means 20 can switch the product output flow into a preconcentration step 40 and a cleanup step 42. An example of this would involve solid phase extraction to concentrate and desalt sample in order to optimize the response of sample output components. Sample output monitoring is accomplished by separating output components with chromatograph 22 and analyzing with mass spectrometer 24. We envision no restriction on the breadth of alternatives for chromatographic separation or mass spectrometry analysis; including, but not limited to MS/MS, ICP/MS, GC/MS, LC/MS, IC/MS, and any number of parallel or serial techniques that are used to character both organic and inorganic species resulting from biological activity. Additionally, this embodiment is intended to incorporate mechanical positioning control 26 of both media input 8 and product output 16 as illustrated in FIG. 3. These components facilitate the positional and temporal control of both input of input media to the sample and output of product output. In this embodiment, a plurality of outputs 16 may be incorporated into the device.

Example 3: Alternate Preferred Embodiment—(Additional Stages with Electrospray Array Output)

The additional arrays, or x-y plane sampling apertures, can also be used for ion generation using atmospheric pressure ionization or desorption ionization electrospray methods.

Figure 5:
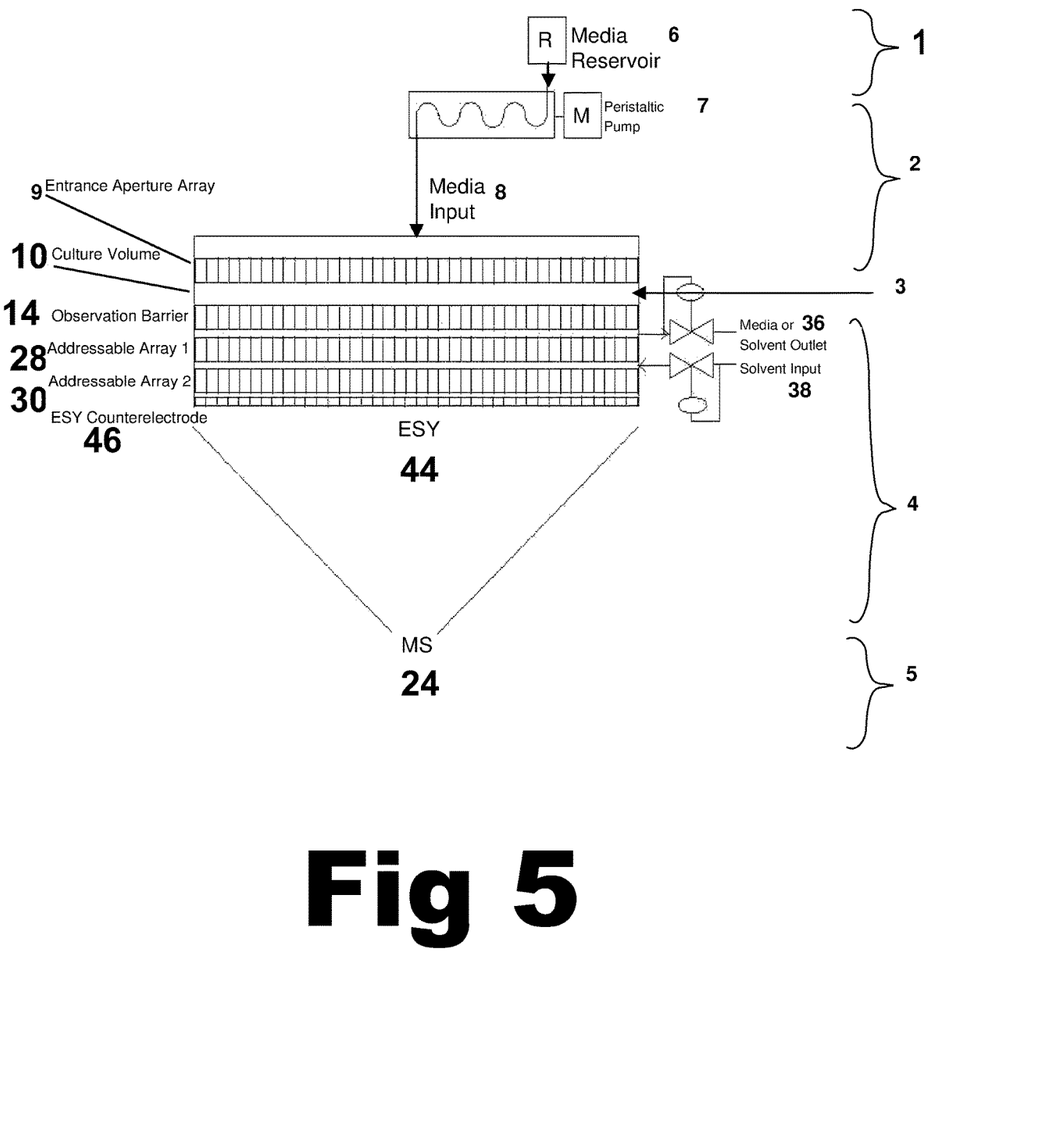

FIG. 5 illustrates a system using two downstream aperture arrays and a x-y translation stage populated with sampling apertures. The system can load sample from the observation barrier through either hydrostatic pressure, electrokinetic, or mechanical means, perform preconcentration and electrophoretic separation of the sample mixture, and optionally perform electrospray ionization if the translation stage sampling aperture comprises a spray nozzle. In this embodiment an exit for the culture media, or downstream solvent, is provided radially at the gap between the observation aperture and addressable array 1. An additional flow stream consisting of an appropriate solvent for analysis and/or preconcentration is introduced radially at the gap between addressable array 1 and addressable array 2. The flows and pressures of the media input and the solvent input can be controlled and switched to generate optimum conditions for a particular sampling state. Addressable array 2 can be used for sample separation using electrophoretic methods.

Figure 6:
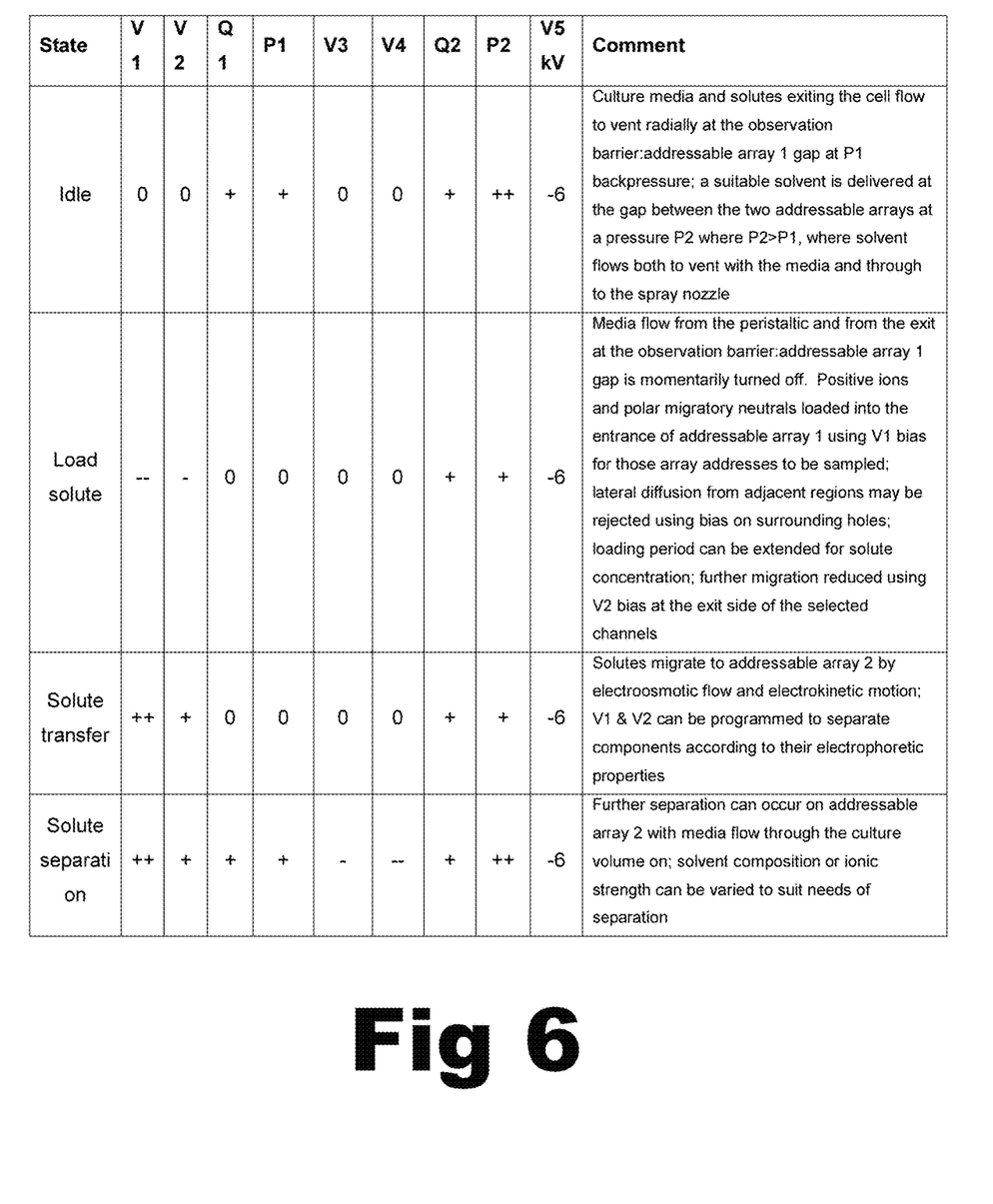
FIG. 6—Table of an example of state conditions for the operation of the preferred embodiment of the invention shown in FIG. 5.

The state table shown in FIG. 6 illustrates one example of the functional modes of the system where sample is preconcentrated, separated, and ionized by electrospray. In this example we show the sampling of positive ions and neutrals capable of migrating toward a negative applied potential. Both addressable arrays are dielectrics and can be controlled at independent potentials.

Rather than using a translational stage for discrete sampling, any embodiment of the device can have as its final stage an array of electrospray nozzles to accommodate each channel of flow, or for combinations of channels. The general use of such a device is based on control of conditions for ion sampling or generation in order to selectively analyze samples. In this case, on a practical basis, to focus ions from such a broad source, such as described and into a single analytical instrument, ion funneling ion optics are used.

This alternate preferred embodiment is schematically illustrated in FIG. 5. The media reservoir 6 containing input media 1 is delivered to sample 3 by input means 2 comprising a peristaltic pump 7. The media input 8 is delivered through entrance aperture array 9 to culture volume 10 containing sample 3. Said sample comprising cells, tissue, or micro-organisms the respond to said input media with biological activity results in absorption of at least some of the input media and subsequently the output of products of said biological activity. The output products are passed through observation barrier 14 whereby output media is directed toward media or solvent outlet 36. This direction of flow can be facilitated by downstream pumping. Some of the products of bio-activity of sample cells may directed away from outlet 36 flow by being induced to pass through addressable array 28. The product species can be induced to flow across the addressable array by electrostatic forces, mechanical forces, and/or pressure. At the downstream side of the addressable array 28 solvent input 38 is accomplished to condition the sample for detection with the mass spectrometer. Solvent input 38 may comprise a wide variety of solvent and solvent modifier alternatives. Said input 38 entrains the product output from addressable array 28 and directs the flow through addressable array 30 to be sampled for downstream monitoring through electrospray needle array 44. Discrete and individually addressable electrospray needles are actuated through applying a needle potential relative to the electrospray counter-electrode 46. Electrospray ionization produces sample product ions that are directed to mass spectrometer 24.

Additional stages in this embodiment may alternatively include conditioning of sample streams to desalt, enrich, and further modify the sample downstream from the sample region with mobile phase components, buffers, modifiers, electrolytes, and ion-pairing reagents. Downstream modification is intended to be completely isolated from the sample environment as to not effect the biological activity of the sample.

Example 4: Additional Preferred Embodiment—(Tubular Bed)

Figure 7A:
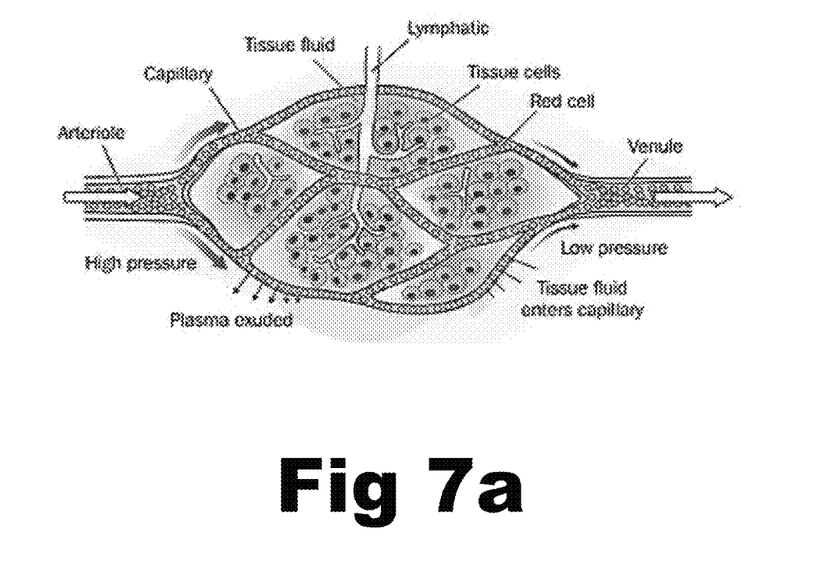
FIG. 7a—Schematic illustration of capillary bed supplying blood to human tissue.
Figure 7B:
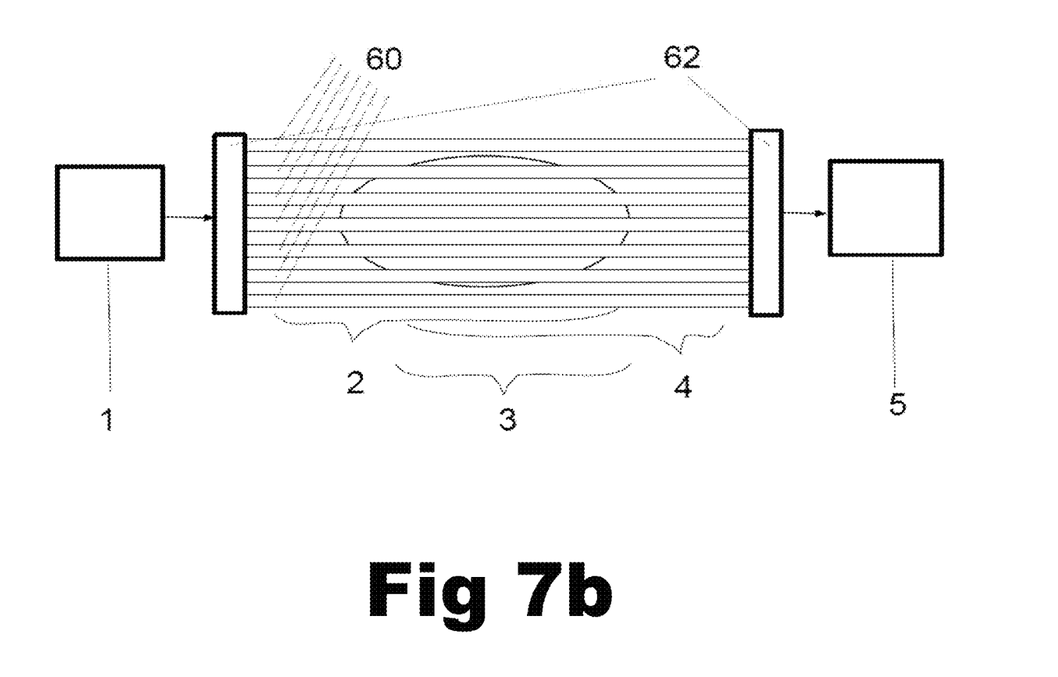
FIG. 7b—An alternative embodiment of the invention utilizing permeable tube bundles to supply input media to the sample cells and monitoring the output stream downstream of the sample region.

An additional preferred embodiment is schematically illustrated in FIG. 7b. With this embodiment input media 1 are pumped into a tubular bed comprising a bundle of permeable tubes 60 connected to the input flow via permeable tube union 62. The sample 3 with this embodiment is interspersed throughout the tubular bed of permeable tubes. The passage of input media and the collection of output products in accomplished by movement out of and into the said tubes. This simple tubular bed device has fluid mechanical and mass transfer similarities to the schematic illustration of a capillary bed supplying blood to human tissue in FIG. 7a. Monitoring means for output from the tubular bed can be accomplished by any number of liquid detection systems, including, but not limited to LC/MS, MS/MS, ICP/MS, GC/MS, and IC/MS.

Example 5: Additional Preferred Embodiment—(Tubular Bed with Isolated Input and Output)

Figure 8:
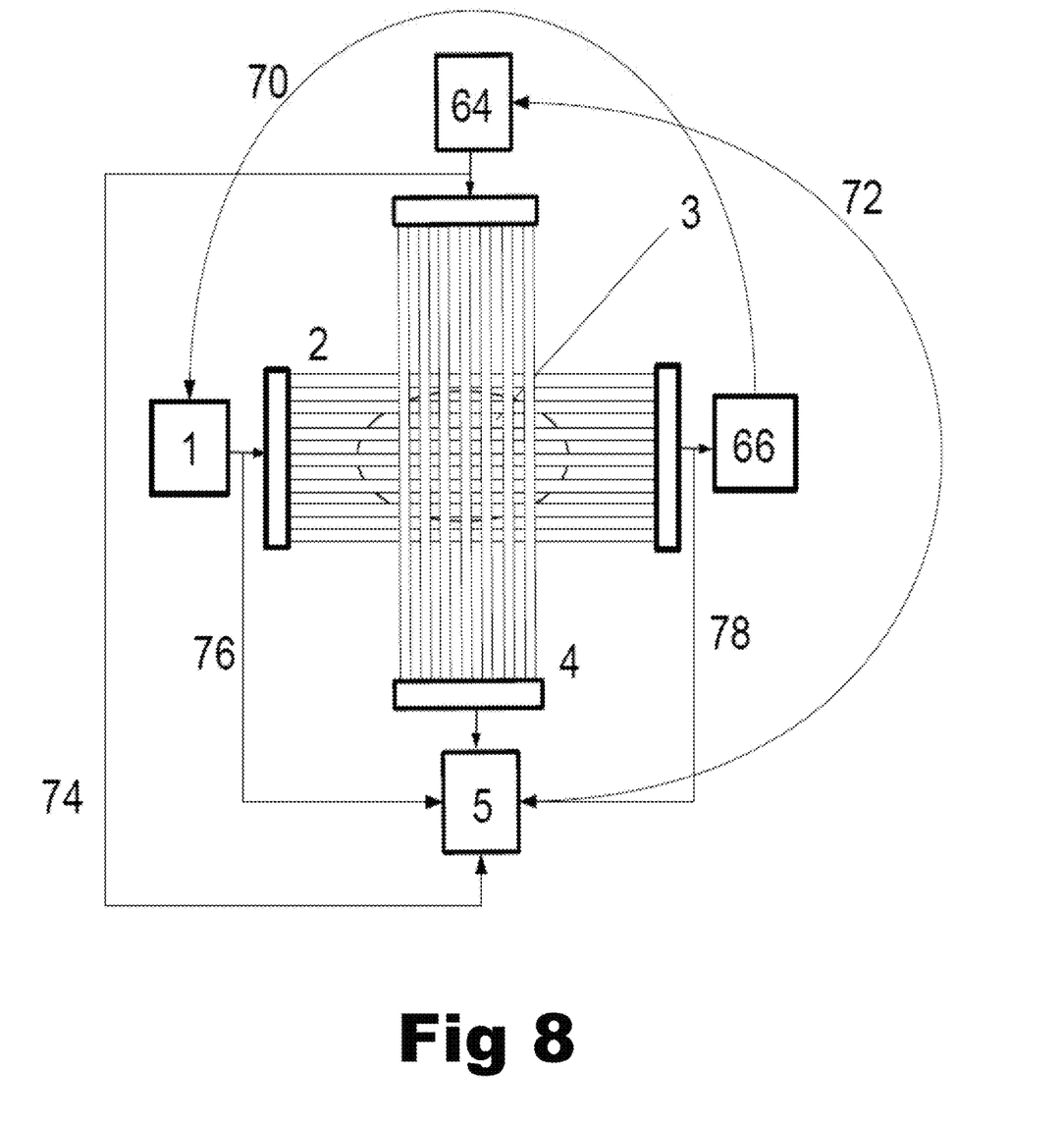
FIG. 8—An alternative embodiment of the invention utilizing permeable tube bundles to supply input media to the sample cells and incorporating a separate monitoring stream to collect and deliver output components with flow and composition independent of the input stream flow and composition. Illustrated are optional recirculation of both inlet streams and monitoring of stream composition from both streams at both inlet and outlet. The results therefrom being alternatively utilized for feedback control.

An additional preferred embodiment is schematically illustrated in FIG. 8. With this embodiment input media 1 are pumped into a tubular bed comprising a bundle of permeable tubes 60 connected to the input flow via permeable tube union 62. The sample 3 with this embodiment is interspersed throughout the tubular bed of permeable tubes. The passage of input media and the collection of output products in accomplished by movement out of and into the said tubes. This more complex tubular bed device incorporates two separate input and output flow streams in contrast to FIG. 7b. The input means 2 is shown as a bed of permeable tubes 60. The output means 4 is shown as a bed of permeable tubes 60 oriented at 90 degrees relative the input means. Sample is interspersed between both input and output bundles in order to have good spatial distributions of input media through the sample and representative spatial collection of the output products of biological activity of the sample. The output means 4 bundles deliver product species to monitoring means 5. In addition, the flow through both input and output streams can be optionally recirculated by recirculation loops 70 and 72. Another option with this embodiment is the addition of collection sampling of input and output streams 74, 76, and 78. The sampling of these streams at various locations before and after the sample enables real-time monitoring of the composition of the stream composition and feedback control of the input media composition based on measured results. The ultimate outcome of this configuration can be real-time closed loop feedback control of the activity of the sample biological activity.

Example 7: Addressable Aperture Array Embodiments—(as Seen in FIGS. 3, 4, and 5)

A component part of FIGS. 3, 4, and 5 are a number of uses of addressable arrays. Addressable arrays are intended to allow controlled transport of sample through a specific aperture within an array of aperture or general transport across the entire array. We envision a number of embodiments for aperture arrays to segregate, control, and select materials moving through the device.

We envision two type of aperture arrays, namely, simple and addressable. Simple arrays are surfaces with a plurality of holes across a transport surface that enable transmission of material from one layer to the next as illustrated in FIG.

9c. There is no selectivity in the x-y dimension with this array 100, however, differential transport can be facilitated by pressure differences (controlling flow between layers) or electrostatics (applying a voltage between metal aperture array separated by an insulator layer. Note that electric fields will only directly influence motion of sample "ions". Indirectly, momentum from moving ions can be imparted to neutral sample species.

Addressable aperture arrays have the added control and flexibility of influencing the transport of material through discrete and selectable apertures across the array surface. We envision a number of alternative embodiments of addressable arrays; including, mechanical and electrostatic control.

Figures 9A, 9B:
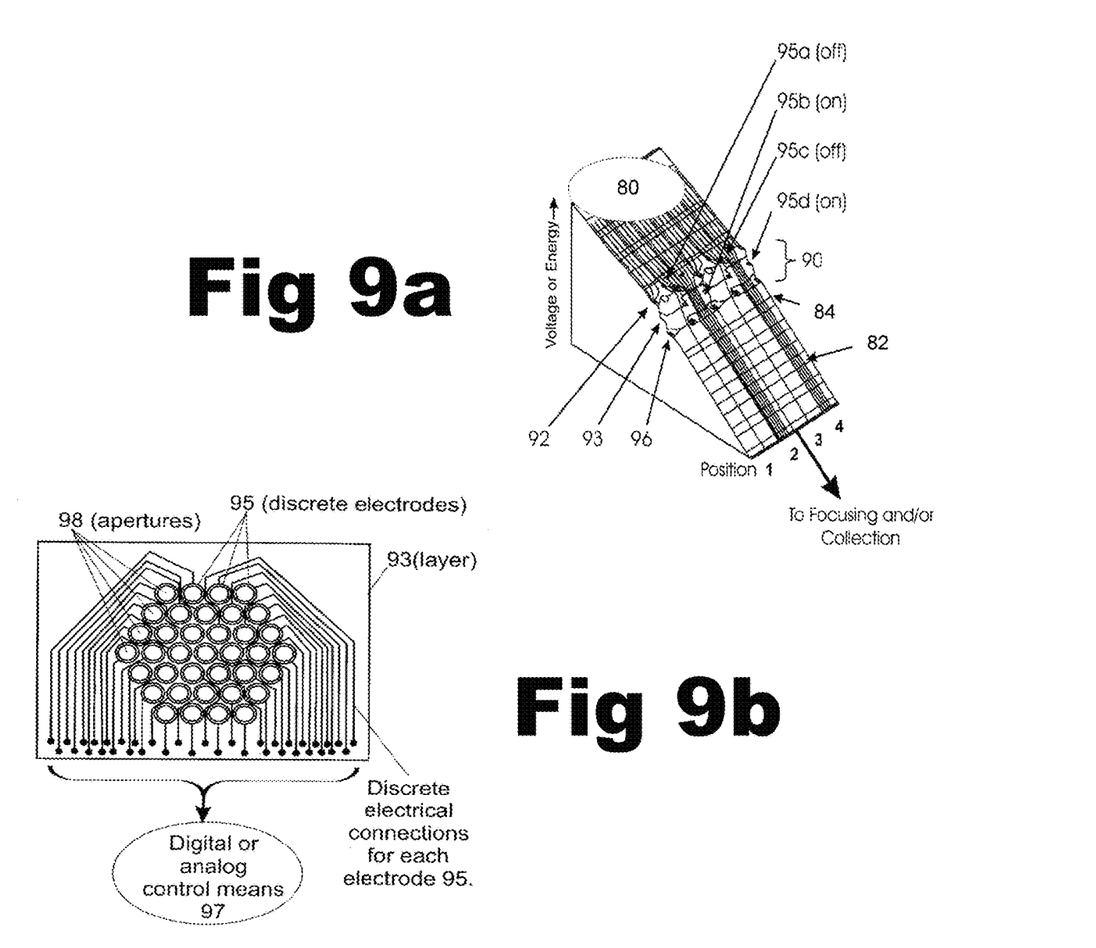
FIG. 9a—An illustration of results from simulation of ion motion through controlled electric fields across one embodiment of an addressable aperture array.
FIG. 9b—An illustration of the electrode layout of an embodiment of an aperture array. Transport of sample solution ions through individual openings in the aperture arrays can be controlled by applying attracting or retarding potentials to the individual electrodes.
Figure 9C:
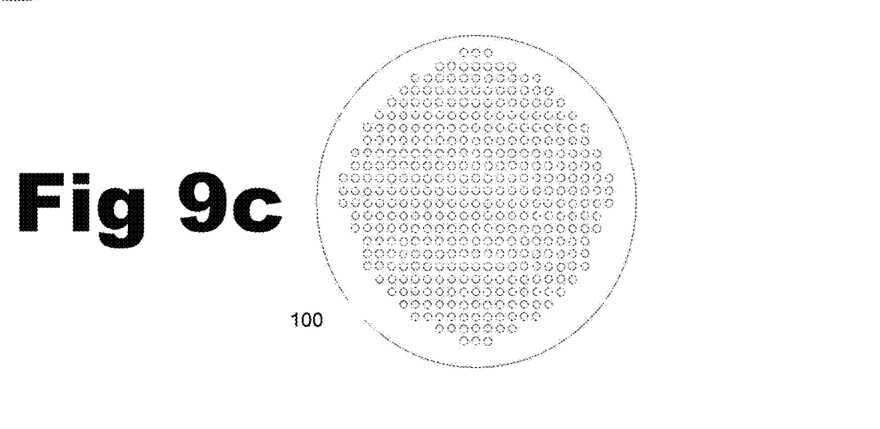
FIG. 9c—An illustration of the top view of a simple aperture array. In this embodiment the openings in the array are not addressable. These arrays function to separate regions of the device and serve to generally direct the flow from one region to the next. Flow across simple aperture arrays can be controlled by applying differential pressures or electric potentials across the arrays.

FIGS. 9a and 9b describe an electrostatically controlled addressable aperture array. With this embodiment sample ions flow through specified apertures based on applied voltages to the specified apertures. (e.g. apertures 1 and 3 do not transmit, apertures 2 and 4 transmit) This illustration shows a three layer aperture array with upstream electrode layer 92, intermediate electrode layer 93, and downstream electrode layer 96. Layer 93 comprises discrete electrodes 95 that can have attracting or repulsing potentials that facilitate transmission of repulsion of sample ions. The combination of three electrode layers is designated as a laminated array. FIG. 9b shows the planar display of the individually addressable discrete electrodes 95 with associated conductance aperture 98. The voltage applied to the discrete electrodes is controlled by control means 97. The three electrode layers of the laminated array are separated by an insulating material that fully defines the conductance pathway through the apertures from upstream to downstream regions. The thickness of the insulating material can be quite substantial and in some device the insulators can be bundles of insulated tubes connecting the layer of the laminate. In the longer tube embodiments, electrophoretic processes can by used to select and separate sample components across the addressable arrays. The simplest addressable arrays lack discrete electrodes but have the ability to attract or repel uniformly across the entire laminate surface.

Mechanically controlled addressable aperture arrays may comprise additional components at each aperture that restrict of facilitate the selective transport of material across the discrete aperture. Alternate modes of gating or valving the apertures will involve the use of micro-valves and piezoelectric materials to open or close apertures. We envision micro-fabrication processes associated with MEMS (micro electrical and mechanical systems) are required to meet the spatial requirements for selective sampling of output products from cell samples.

Sample Embodiments

Samples interrogated with this invention include, but are not limited to cells, tissues, micro-organisms, cell cultures, tissue cultures, viruses, bacteria, collected samples from a biological (e.g. bio-hazards or bio agents), and cells supported upon a substrate material. We envision homogeneous biological samples to be evaluated by precise spatial and temporal monitoring under controlled input of input media, allowing both spatial and temporal information about the sample activity. It is important to note that one mode of operation of this invention with homogeneous samples will include differential input of input media across the sample volume in order to test differential response to said input media by the sample; as measured by the differential spatial and temporal measurement of output products. Applications to drug dosing studies or toxicity studies for a given cell line apply to this embodiment.

In addition, interrogation of samples may also include heterogeneous composition of sample applied to the sample observation window in order to evaluate differential response from varied cell or tissue types to uniform input media application. This application would certainly have applications in tissue imaging studies, as well as interrogation of wild and variant cell lines. Any combination of sample variability and input variability may be applied to application of this invention to solve problems in studying living cell behavior.

Other applications for samples that do not include living cells are envisioned for monitoring 2-dimensional and 3-dimensional samples for spatial and temporal imaging. An example of this would involve the inclusion of 2-D gels containing separated components from a cell lysate in order to extract and characterize gel sample components by transferring then downstream (z-dimension) for further conditioning and analysis (e.g. enzymatic digest and sequencing).

Non-biological samples can also be evaluated for temporal and spatial composition. An example would be the evaluation and interrogation of catalytic surfaces under time and space varying conditions.

Geometric Considerations of Preferred Embodiments

The general concept of the current invention is to allow local and controlled input of various media to cell cultures and tissues while also maintaining precise local collection of output products from biological activity. The present preferred embodiments illustrate two approaches; namely, laminar and tubular. It is the intent of this invention not to limit the geometries to the illustrated embodiments; but to further disclose that combinations of sample geometries that incorporate both laminar and tubular input, sample, and output components will serve to address the sampling needs for some set of sampling applications. We envision, for example, incorporating tubular beds into the sampling region of a laminar device. This added input or output capability will have advantages for some cell types of sample geometries. We also envision geometries that may conform to sample characteristics that are neither laminar or tubular.

CITATIONS (1) U.S. Pat. No. 5,808,300; August 1998; Caprioli, Appl May 1997, U.S. Pat. No. 854,040.
(2) Hu K, Ahmadzadeh H, Krylov S N, *Anal Chem* 2004, 76(13), 3864-6.
(3) Boardman A, McQuaide S C, Zhu C, Whitmore C, Lidstrom M E, Dovichi N J, *Anal Chem.* 2008, 80(19), 7631-4.
(4) Wang Y, Hong J, Cressman E N K, Arriaga E A, *Anal Chem.* 2009, 81(9), 3321-8.
(5) U.S. Pat. No. 7,831,075 B2; November 2010; Wilson et al, Appl October 2006, Ser. No. 11/581,995.
(6) U.S. Pat. No. 7,442,927; October 2008; Fedorov, Appl January 2006, Ser. No. 11/336,137.
(7) "Culture of Animal Cells", 6$^{th}$ Edition, R. Ian Freshney, John Wiley & Sons, Inc., 2010, ISBN 978-0-470-52812-9.
(8) Jung B, Bharadwaj R, Santiago J G, Electrophoresis, 2003, 24, 3476-83.

(9) Heineman W R, Gong M, Wehmeyer K R, Limbach P A, Arias F, *Anal Chem.* 2006, 78, 3730-7.

The invention claimed is:

1. An apparatus for spatial and temporal, monitoring, analysis, and chemical mapping of a living cell aggregate, comprising:
   a culture volume containing the living cell aggregate, the living cell aggregate comprising one or more aggregate regions,
   an addressable and controllable input barrier comprising a plurality of apertures in fluid communication with the culture volume and configured to provide fluidic control of input media into the culture volume, such that selective and differential input media is delivered to at least one of the one or more aggregate regions,
   an addressable and controllable output barrier comprising a plurality of apertures, each of the plurality of apertures of the output barrier corresponding to at least one of the plurality of apertures of the input barrier proximate a same region of the living cell aggregate, wherein each of the plurality of apertures of the output barrier is configured to receive extracellular fluidic output comprising a product of biological activity resulting from the living cell aggregate responding to the input media provided to the corresponding at least one of the plurality of apertures of the input barrier, and
   an analyzer in fluid communication with the output barrier and configured to analyze the extracellular fluidic output
   from each of the plurality of apertures of the output barrier individually, wherein the analyzer is configured to generate a chemical map of the living cell aggregate based on individual analysis results performed on the extracellular fluidic output from each of the plurality of apertures of the output barrier.

2. The apparatus as described in claim 1, wherein the living cell aggregate comprises one of the group of cells, tissues, micro-organisms, cell cultures, tissue cultures, viruses, bacteria, and stem cells.

3. The apparatus as described in claim 1, wherein the input media comprises a reagent, nutrient, drug, gas, blood, output from upstream cultures, output from natural environments, buffer, stimulant, retardant, or pollutant, wherein the input media induces a chemical or physical response from or supports growth of the living cell aggregate.

4. The apparatus as described in claim 1, wherein a differential input of the input media is configured to be delivered to the input barrier by mechanical means.

5. The apparatus as described in claim 1, wherein a differential input of the input media is configured to be delivered to the input barrier by electro-fluidic means.

6. The apparatus as described in claim 1, wherein the analyzer comprises a sample collection device, a sample separation device, a sample component analyzer with mass spectrometry, ion mobility, or alternate molecular detection technology, or a sample component analyzer with absorption or emission spectroscopy.

7. The apparatus as described in claim 1, wherein the output barrier comprises addressable laminated aperture arrays that provide discrete and controllable pathways for collecting the extracellular fluidic output from the living cell aggregate for precise spatially and temporally controllable collection of the extracellular fluidic output.

8. The apparatus as described in claim 1, wherein cellular behavior of the living cell aggregate is further controlled by adjusting a composition of the input media delivered to one or more of the aggregate regions based on results from the analyzer.

9. The apparatus as described in claim 1, wherein cellular behavior is monitored by the analyzer analyzing the extracellular fluidic output of one or more of the aggregate regions based on a response of the living cell aggregate to a composition of the input media.

10. The apparatus as described in claim 1, wherein the extracellular fluidic output is further extracted into an analytical solvent flow across the output barrier to prevent analytical solvents and reagents from degrading the living cell aggregate.

11. The apparatus as described in claim 1, wherein the extracellular fluidic output is directly introduced into the analyzer.

12. The apparatus as described in claim 1, wherein the extracellular fluidic output from one or more of the aggregate regions is collected, extracted, separated, pre-treated or conditioned before being introduced into the analyzer.

13. The apparatus of claim 1, wherein the input barrier comprises an aperture array addressed or controlled to produce multiple input pathways for variable input media to be delivered to the living cell aggregate on a spatially or temporally resolved basis using the aperture array.

14. The apparatus of claim 1, wherein the output barrier is configured to extract the extracellular fluidic output differentially and using electro-fluidic means.

15. The apparatus of claim 1, wherein the output barrier is configured to extract the extracellular fluidic output differentially and using mechanical means.

16. The apparatus of claim 1, wherein the living cell aggregate comprises a heterogeneous composition of cell types, such that differential responses of the cell types can be determined in response to a spatially resolved input and cell-cell signaling measured.

17. The apparatus of claim 1, wherein the culture volume comprises a scaffold configured to promote cellular adherence and three-dimensional cellular growth of the living cell aggregate.

18. The apparatus of claim 1, wherein a geometry of the input barrier and the output barrier conforms to a tubular geometry of a vascular system or capillary bed.

19. The apparatus of claim 1, wherein the output barrier comprises a permeable material positioned upstream relative to the plurality of apertures of the output barrier, the permeable material configured for selective passage of the extracellular fluidic product.

20. The apparatus of claim 1, wherein the output barrier comprises an aperture array addressed or controlled to produce segmented flow to multiple output pathways in fluid communication with the analyzer on a spatially and temporally resolved basis.

21. The apparatus of claim 1, wherein the input barrier comprises an array of tubes addressed and controlled using mechanical or electro-fluidic means to produce multiple input pathways for variable input media to be delivered to the living cell aggregate on a spatially and temporally resolved basis.

22. The apparatus of claim 1, wherein the output barrier comprises an array of tubes addressed and controlled using mechanical or electro-fluidic means to produce multiple output pathways.

23. The apparatus of claim 1, wherein additional input and output streams are positioned orthogonal to the input barrier and the output barrier and further conform to a tubular geometry, and are interposed in the culture volume so as to enable additional dosing or extractive processes into and out of the culture volume.

\* \* \* \* \*

UNITED STATES PATENT AND TRADEMARK OFFICE
CERTIFICATE OF CORRECTION

PATENT NO. : 10,852,296 B2
APPLICATION NO. : 13/728865
DATED : December 1, 2020
INVENTOR(S) : James D. Buchner, Sr. et al.

Page 1 of 1

It is certified that error appears in the above-identified patent and that said Letters Patent is hereby corrected as shown below:

On the Title Page

Column 2, Other Publications, Line 1, delete "cappilaries" and insert -- capillaries --

Signed and Sealed this
First Day of June, 2021

Drew Hirshfeld
*Performing the Functions and Duties of the*
*Under Secretary of Commerce for Intellectual Property and*
*Director of the United States Patent and Trademark Office*